US012605313B2

(12) United States Patent
Puigdelloses Ferrer et al.

(10) Patent No.: US 12,605,313 B2
(45) Date of Patent: Apr. 21, 2026

(54) COMPOSITIONS FOR DYEING KERATIN FIBERS

(71) Applicant: Revlon Consumer Products Corporation, New York, NY (US)

(72) Inventors: Blanca Puigdelloses Ferrer, Barcelona (ES); Alex Tinarelli, San Giovanni (IT); Julieta Paola Nava Mendoza, Aveiro (PT); Olga Colom Vives, La Granada (ES)

(73) Assignee: Revlon Consumer Products Corporation, New York, NY (US)

( * ) Notice: Subject to any disclaimer, the term of this patent is extended or adjusted under 35 U.S.C. 154(b) by 1200 days.

(21) Appl. No.: 17/296,338

(22) PCT Filed: Nov. 26, 2019

(86) PCT No.: PCT/IB2019/001208
§ 371 (c)(1),
(2) Date: May 24, 2021

(87) PCT Pub. No.: WO2020/109859
PCT Pub. Date: Jun. 4, 2020

(65) Prior Publication Data

US 2022/0016445 A1 Jan. 20, 2022

(30) Foreign Application Priority Data

Nov. 28, 2018 (EP) .................................... 18382862

(51) Int. Cl.

| | |
|---|---|
| ***A61Q 5/10*** | (2006.01) |
| ***A61K 8/22*** | (2006.01) |
| ***A61K 8/34*** | (2006.01) |
| ***A61K 8/41*** | (2006.01) |
| ***A61K 8/46*** | (2006.01) |
| ***A61K 8/86*** | (2006.01) |

(52) U.S. Cl.
CPC ................ *A61K 8/22* (2013.01); *A61K 8/342* (2013.01); *A61K 8/416* (2013.01); *A61K 8/463* (2013.01); *A61K 8/86* (2013.01); *A61Q 5/10* (2013.01); *A61K 2800/26* (2013.01); *A61K 2800/4324* (2013.01); *A61K 2800/596* (2013.01); *A61K 2800/882* (2013.01)

(58) Field of Classification Search
CPC ........................................................ A61Q 5/10
See application file for complete search history.

(56) References Cited

U.S. PATENT DOCUMENTS

| | | | | |
|---|---|---|---|---|
| 8,795,391 B2 * | 8/2014 | Iizaki | ........................ | A61Q 5/10 |
| 2015/0101129 A1 * | 4/2015 | Schmenger | .............. | A61K 8/34 |
| 2018/0263881 A1 | 9/2018 | Schoepgens et al. | | |

FOREIGN PATENT DOCUMENTS

| | | | | |
|---|---|---|---|---|
| EP | 2578671 A1 | 4/2013 | | |
| EP | 2859880 A1 | 4/2015 | | |
| EP | 3360537 A1 | 8/2018 | | |
| EP | 3033068 B1 * | 11/2018 | ............... | A61K 8/24 |
| EP | 3659578 A1 | 6/2020 | | |
| WO | 2011024300 A1 | 3/2011 | | |
| WO | 2012032673 A1 | 3/2012 | | |
| WO | 2020109859 A1 | 6/2020 | | |

OTHER PUBLICATIONS

TGSC Information System, Ceteareth-5, The Good Scents Company [online], [retrieved on Aug. 20, 2024]. Retrieved from the Internet <URL: https://www.thegoodscentscompany.com/data/rw1369461.html> (Year: 2024).*

Stearoxypropyltrimonium chloride, CID 18519353, National Library of Medicine, PubChem [online], [retrieved on Aug. 20, 2024]. Retrieved from the Internet <URL: https://pubchem.ncbi.nlm.nih.gov/compound/23328-71-4> (Year: 2024).*

SpecialChem, Ceteareth-20, INCI Directory, downloaded in Apr. 2025 (Year: 2025).*

Extended European Search Report received for European Patent Application No. 18382862.3, issued on Jun. 4, 2019, 10 pages.

International Search Report and Written Opinion received for International Patent Application No. PCT/IB2019/001208, mailed on Feb. 17, 2020, 12 pages.

Communication pursuant to Article 94(3) EPC issued in European Patent Application No. 19824195.2, mailed on Jan. 31, 2024, 7 pages.

"Colourant Cream Kit", Mintel, Product Listing, 8 pages, retrieved from http://www.gnpd.com, Jul. 25, 2012.

"Hair Colourant Cream", Mintel, Product Listing, 8 pages, retrieved from http://www.gnpd.com, Feb. 9, 2016.

Brown , "Hair Coloring", Chapter 7 of Hair and Hair Care, Cosmetic Science and Technology Series, vol. 17, pp. 191-215, 1997, Marcel Dekker.

(Continued)

*Primary Examiner* — Robert A Wax

(74) *Attorney, Agent, or Firm* — Dorsey & Whitney LLP

(57) ABSTRACT

Compositions for dyeing keratin fibers are described. These dyeing compositions comprise, in a cosmetically acceptable medium, based on the total weight of the composition: (a) at least one anionic surfactant, (b) at least one cationic surfactant; (c) at least one alkoxylated $C_6$-$C_{24}$ fatty alcohol; (d) at least one $C_6$-$C_{24}$ fatty alcohol; (e) at least one oxidation dye, (f) about 0.1-10 wt. % of ammonia; wherein the compositions do not comprise more than 2 wt. % of alkanolamines, $C_1$-$C_4$ alkyl alkanolamines, or any fatty acid salt thereof, or mixtures thereof. These dyeing compositions present reduced ammonia odor and, at the same time, a faster color processing. A process for preparing these compositions, a process for permanent dyeing keratin fibers using these compositions and a packaging kit containing these compositions are also described.

11 Claims, No Drawings

(56) References Cited

OTHER PUBLICATIONS

"Ammonium Bicarbonate", Monograph, retrieved from https://incipedia.personalcarecouncil.org/monograph/?id=36fc78db-7c7c-4760-a5d5-7c9ab854422b; retrieved on May 8, 2025.
"Guanidine Carbonate", Monograph, retrieved from https://incipedia.personalcarecouncil.org/monograph/?id=2547da1d-3de3-4863-a066-1576b602000c, retrieved on May 8, 2025.
"PH Adjusters", Personal Care Products Council, Ingredient Information Lists, retrieved on May 8, 2025, retrieved from https://incipedia.personalcarecouncil.org/sub-lists/sub-list-details/?id=157a4551-9c82-ec11-8d21-000d3a98a506&reportedfunctioninitvalue=.

* cited by examiner

COMPOSITIONS FOR DYEING KERATIN FIBERS

This application claims priority to International Patent Application No. PCT/IB2019/001208, filed Nov. 26, 2019, entitled "COMPOSITIONS FOR DYEING KERATIN FIBERS," which in turn claims priority to European Application No. 18382862.3, filed Nov. 28, 2018, entitled "COMPOSITIONS FOR DYEING KERATIN FIBERS", each of which is incorporated by reference herein, in the entirety and for all purposes.

TECHNICAL FIELD

Compositions for dyeing keratin fibers are described. Said dyeing compositions comprise, in a cosmetically acceptable medium, based on the total weight of the composition: (a) at least one anionic surfactant, (b) at least one cationic surfactant; (c) at least one alkoxylated $C_6$-$C_{24}$ fatty alcohol; (d) at least one $C_6$-$C_{24}$ fatty alcohol; (e) at least one oxidation dye, (f) about 0.1-10 wt. % of ammonia; wherein the compositions do not comprise more than 2 wt. % of alkanolamines, $C_1$-$C_4$ alkyl alkanolamines, or any fatty acid salt thereof, or mixtures thereof. These dyeing compositions present reduced ammonia odor and, at the same time, a faster color processing.

BACKGROUND

The information provided below is not admitted to be prior art to the present disclosure, but is provided solely to assist the understanding of the reader.

It is known for centuries to dye keratinous fibres, for example human hair, with dyeing compositions comprising dyes or dye precursors.

Most hair dyeing products fall under three major groupings: temporary hair dyeing, semi-permanent hair dyeing, and permanent hair dyeing.

Temporary hair dyeing is usually a leave on product that causes minimal damage to the hair. However, temporary hair dyeing causes stains, and leaches out under rain or with perspiration. Temporary hair dyeing washes out with the next shampoo.

Semi-permanent hair dyeing comes as a rinse, and it causes minimal damage to the hair. However, semi-permanent hair dyeing washes out to some degree with each shampoo and washes out completely within about 4 to 6 shampoos.

Permanent hair dyeing is characterized by excellent, long-lasting color results. It generally comes in two parts: a dye solution and a developer solution, which contains an oxidizing agent such as, for example, hydrogen peroxide. Usually, permanent hair dyeing compositions do not contain dyestuffs in the conventional sense of the word. They contain colourless precursors which will react with the oxidizing agent inside the hair fibre to produce coloured molecules. The dye solution and the developer solution are mixed and then applied to the hair, which is then left for about 10 to about 50 minutes and then rinsed with water.

The oxidizing agent (e.g., hydrogen peroxide) initiates not only the formation of the dyes, but it also breaks down oxidatively the hair's own color pigments (melanins), so a lightening coloring is also possible simultaneously. In order to produce satisfactory coloring and lightening, permanent hair dyeing usually require an alkaline pH during use; optimal results are achieved in particular at pH values between about 8 and 12.

Ammonia is the alkalizing agent of choice today for adjusting these pH values. Not only can the pH range necessary for dye formation be adjusted with ammonia, but ammonia also causes the swelling of hair to a greater degree than all other known alkalizing agents. At the same time, ammonia acts as a penetration agent or penetration aid, also to a greater extent than all other commercial alkalizing agents.

For these reasons, more intensive colors and significantly better gray coverage are obtained during use of ammonia in permanent hair coloration in comparison with other alkalizing agents (such as, for example, potassium or sodium hydroxide, alkanolamines, or carbonates such as sodium carbonate or potassium carbonate).

The performance advantages associated with the use of ammonia are so diverse that ammonia is used in a great number of permanent hair coloration despite its unpleasant, pungent odor.

Extensive efforts to reduce the ammonia odor are already known from the literature. In this regard, there are different options for minimizing the odor: The literature gives as the first option the variation of the alkalizing agent and thereby the partial or total replacement of ammonia by odorless alternatives.

Thus, for example, there are a great number of formulations in which a mixture of ammonia and monoethanolamine or monoethanolamine alone is used as the alkalizing agent. A reduction in the ammonia content, however, generally results in a poorer penetration of the dyes into the hair, which as previously described is reflected particularly in poorer gray coverage.

A second option for reducing the ammonia odor is the addition of special perfume substances, which are intended to cover the ammonia odor. Perfume substances can be unstable under alkaline storage conditions, however, so that there is the risk that the aromatic substances are broken down or changed structurally during storage, which is also reflected in an unpredictable change in the odor.

Other option for reducing the ammonia odor is to increase the addition of standard perfume substances, which cover the ammonia odor. However, perfume substances are known to cause allergic reactions. Thus, increasing the amount of these substance may increase the risk of allergic reactions to the consumers.

Accordingly, there is a need for compositions for dyeing keratin fibers with a reduced ammonia odor and, at the same time, with a faster color processing to decrease hair damage and richer color uptake.

SUMMARY

Described herein is a composition for dyeing keratin fibers comprising, in a cosmetically acceptable medium, based on the total weight of the composition: (a) at least one anionic surfactant, (b) at least one cationic surfactant; (c) at least one alkoxylated $C_6$-$C_{24}$ fatty alcohol; (d) at least one $C_6$-$C_{24}$ fatty alcohol; (e) at least one oxidation dye, (f) about 0.1-10 wt. % of ammonia; wherein the composition does not comprise more than 2 wt. % of alkanolamines, $C_1$-$C_4$ alkyl alkanolamines, or any fatty acid salt thereof, or mixtures thereof.

An embodiment disclosed herein is a dyeing composition as defined above comprising, in a cosmetically acceptable medium, based on the total weight of the composition: (a) at least one anionic surfactant; (b) at least one cationic surfactant; (c) at least one alkoxylated $C_6$-$C_{24}$ fatty alcohol; (d) at least one $C_6$-$C_{24}$ fatty alcohol; (e) about 0.001-10 wt. % of at least one oxidation dye; (f) about 0.2-7.5 wt. % of ammonia; wherein the composition does not comprise more than 2 wt. % of alkanolamines, $C_1$-$C_4$ alkyl alkanolamines, or any fatty acid salt thereof, or mixtures thereof.

In an embodiment disclosed herein the composition for dyeing keratin fibers does not comprise more than 0.2 wt. % of alkanolamines, $C_1$-$C_4$ alkyl alkanolamines, or any fatty acid salt thereof, or mixtures thereof.

In an embodiment disclosed herein ammonia is the only alkalizing agent present in dyeing the composition.

In an embodiment disclosed herein the at least one anionic surfactant is selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof.

In an embodiment disclosed herein the at least one anionic surfactant is selected from alkyl ether carboxylates, alkyl ether sulfates, olefin sulfonates, and mixtures thereof.

In an embodiment disclosed herein the at least one cationic surfactant is selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof.

In an embodiment disclosed herein the at least one cationic surfactant is selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof.

In an embodiment disclosed herein the at least one alkoxylated $C_6$-$C_{24}$ fatty alcohol is selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof, and mixtures thereof.

In an embodiment disclosed herein the at least one $C_6$-$C_{24}$ fatty alcohol is selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof.

An embodiment disclosed herein is a dyeing composition as defined above comprising, in a cosmetically acceptable medium, based on the total weight of the composition:

a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;
c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof, and mixtures thereof;
d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;
e) about 0.001-10 wt. % of at least one oxidation dye;
f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In an embodiment disclosed herein the keratin fibers are human hair.

In an embodiment disclosed herein the dyeing composition exhibits optical anisotropy.

An embodiment disclosed herein is a process for preparing a dyeing composition as defined above comprising the steps of:

i) adding (a) at least one anionic surfactant, (c) least one alkoxylated $C_6$-$C_{24}$ fatty alcohol, (d) at least one $C_6$-$C_{24}$ fatty alcohol and (e) at least one oxidation dye to a water phase at a temperature from about 50° C. to about 90° C. and under agitation;
ii) cooling the emulsion obtained in step (i) to a temperature from about 30° C. to about 50° C. and under agitation;
iii) adding (b) at least one cationic surfactant and (f) ammonia to the emulsion obtained in step (ii) under agitation.

An embodiment disclosed herein is a dyeing composition for dyeing keratin fibers obtained by a process as defined above.

An embodiment disclosed herein is a process for the permanent dyeing of keratin fibers comprising the steps of:

i) mixing, before application, a composition for dyeing keratin fibers as defined above, with a hydrogen peroxide composition, to form a ready-to-use composition;
ii) applying the ready-to-use composition obtained in step (i) to the keratin fibers for a period which is sufficient to obtain the dyeing effect;
iii) removing the ready-to-use composition from the keratin fibers by rinsing with water.

In embodiment disclosed herein, the process for the permanent dyeing of keratin fibers is intended for reducing the difference in color between the roots and the dyed keratinous fiber and/or or to rejuvenate the color of the fibers.

An embodiment disclosed herein is a multi-compartment device for dyeing keratin fibers comprising at least two compartments packaged separate from one another, wherein one compartment comprises a composition for dyeing keratin fibers as defined above and a second compartment comprises a hydrogen peroxide composition.

DETAILED DESCRIPTION

Embodiments of the present disclosure are discussed in detail below. In describing embodiments, specific terminology is employed for the sake of clarity. However, the disclosure is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the disclosure. While a number of embodiments and features are described herein, it is to be understood that the various features of the disclosure and aspects of embodiments, even if described separately, may be combined unless mutually exclusive or contrary to the specific description. All references cited herein are incorporated by reference as if each had been individually incorporated.

The terms "about" or "approximately" as used herein shall generally mean within 10 percent of a given value. Other than in the operating examples, or where otherwise indicated, all numbers expressing quantities of ingredients and/or reaction conditions are to be understood as being modified in all instances by the term "about".

The term "keratin fibers" as used herein refers to a family of proteins that occur in the vertebrates and exercise a protective function. In an embodiment, keratin fibers refers to human keratin fibers. In another embodiment, keratin fibers refers to human hair.

The term "comprising" refers to optional compatible components/steps that can be used provided that the important ingredients/steps are present.

The term "comprising" thus encompasses and includes the more restrictive terms "consisting of" and "consisting essentially of".

"Optical anisotropy" is a phenomenon that is observed when the speed of light in a medium depends from the polarization plane of the electromagnetic wave in the medium.

Isotropic and anisotropic materials can be distinguished by polarized light microscopy.

The optical properties of anisotropy can provide information on the structure and composition of materials such as lipid vesicles, microemulsions and liquid crystalline systems.

Since the isotropic materials have only one refractive index and no restriction on the vibration plane of light passing through them so they have the same optical properties in all directions.

Then, under polarized light isotropic materials are characterized by a dark field. Moreover, anisotropic material have optical properties that change with the orientation of the incident light in relation to crystallographic axes showing different refractive indices depending of the direction of propagation of light through the system and on the orientation of the vibration plane. Then, due to its molecular organization, the anisotropic systems display Malta crosses under polarized light.

The term "alkanolamines" as used herein refers to chemical compounds that contain both hydroxyl (—OH) and amino functional groups on an alkane backbone.

The term "alkyl alkanolamines" as used herein refers chemical compounds that contain a basic secondary or tertiary nitrogen atom and at least one hydroxyl group.

Typically, the composition for dyeing keratin fibers comprises, in a cosmetically acceptable medium, based on the total weight of the composition: (a) at least one anionic surfactant, (b) at least one cationic surfactant; (c) at least one alkoxylated $C_6$-$C_{24}$ fatty alcohol; (d) at least one $C_6$-$C_{24}$ fatty alcohol; (e) at least one oxidation dye, (f) about 0.1-10 wt. % of ammonia; wherein the composition does not comprise more than 2 wt. % of alkanolamines, $C_1$-$C_4$ alkyl alkanolamines, or any fatty acid salt thereof, or mixtures thereof.

In an embodiment disclosed herein, the composition for dyeing keratin fibers does not comprise, based on the total weight of the composition, more than 0.2 wt. % of alkanolamines, $C_1$-$C_4$ alkyl alkanolamines, or any fatty acid salt thereof, or mixtures thereof.

In an embodiment disclosed herein ammonia is the only alkalizing agent present in the dyeing composition, i.e. it is free from any alkanolamines and $C_1$-$C_4$ alkyl alkanolamines or any fatty acid salt thereof, or mixtures thereof.

Cosmetically Acceptable Medium

The cosmetically acceptable medium for the dyeing composition is typically an aqueous medium consisting of water and may advantageously contain cosmetically acceptable organic solvents including more particularly alcohols such as ethyl alcohol, isopropyl alcohol, benzyl alcohol and phenylethyl alcohol, glycols or glycol ethers such as, for example, monomethyl, monoethyl and monobutyl ethers of ethylene glycol, propylene glycol or its ethers such as, for example, monomethyl ether of propylene glycol, butylene glycol, dipropylene glycol as well as the alkyl ethers of diethylene glycol such as for example monoethyl ether or monobutyl ether of diethylene glycol. Water may be present in the range of about 30 to about 90 wt. %, or about 40 to about 85 wt. %, or about 45 to about 80 wt. %, based on the total weight of the composition. The organic solvents may then be present in concentrations of between about 0.5 and 20 wt. %, or about 2 and 15 wt. %, based on the total weight of the composition.

The Anionic Surfactant

As indicated above, the composition for dyeing keratin fibers may comprise (a) at least one anionic surfactant. Examples of suitable anionic surfactants include, but are not limited to, alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof. Typically, the at least one anionic surfactant is selected from alkyl ether carboxylates, alkyl ether sulfates, olefin sulfonates, and mixtures thereof.

Alkyl ether carboxylates are obtained by ethoxylation and subsequent carboxymethylation of fatty alcohols (preferably having 6 to 24 carbon atoms). The process is divided into two steps. The first one is the ethoxylation of alcohols under standard conditions known by the skilled in the art. However, one may also start from commercially available ethoxylated alcohols.

In the second step, the ethoxylated alcohols are reacted with a strong base, such as sodium or potassium hydroxide, in presence of a reducing agent, e.g., sodium borohydride, to obtain the corresponding alkoxylate, which is carboxymethylated with sodium monochloroacetate (SMCA).

Optionally, the crude alkyl ether carboxylate can be purified by first converting the crude products with hydrochloric acid or sulphuric acid into the free acid. Said acid is washed and after that it is converted into the corresponding salt.

Examples of suitable alkyl ether carboxylates include, but are not limited to, Potassium Laureth-4 Carboxylate, Sodium Laureth-4 Carboxylate, Sodium Laureth-5 Carboxylate, Sodium Laureth-6 Carboxylate, and Sodium Laureth-11 Carboxylate.

Alkyl ether sulfates are obtained by the sulfonation of an ethoxylated alcohol. Examples of suitable alkyl ether sulfates include, but are not limited to, Ammonium Laureth Sulfate, Monoethanolamine (MEA)-Laureth Sulfate, Monoisopropanolamine (MIPA)-Laureth Sulfate, Sodium Laureth Sulfate, and Triethanolamine (TEA)-Laureth Sulfate; particularly Sodium Laureth Sulfate having an average degree of ethoxylation of about 1 to 3.

Olefin sulfonates are can be produced by sulfonation of an alpha olefin by means of 35 uncomplexed sulfur trioxide, followed by neutralization of the acid reaction mixture in conditions such that any sultones which have been formed in the reaction are hydrolyzed to give the corresponding hydroxy-alkanesulfonates. Examples of suitable olefin sulfonates include, but are not limited to, $C_{14}$-$C_{16}$ Olefin Sulfonate salts, such as Sodium $C_{14}$-$C_{16}$ Olefin Sulfonate.

Typically, in the composition for dyeing keratin fibers, the total amount of (a) the at least one anionic surfactant is in the range of about 0.1 to about 25 wt. %, or about 0.3 to about 15 wt. %, or about 0.5 to about 10 wt. %, based on the total weight of the composition.

The Cationic Surfactant

As indicated above, the composition for dyeing keratin fibers may comprise (b) at least one cationic surfactant. Examples of suitable cationic surfactants include, but are not limited to, alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof. Typically, the at least one cationic surfactant is selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof.

Examples of suitable $C_6$-$C_{24}$ alkyl trimethyl quaternary ammonium salts include, but are not limited to, Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, and mixtures thereof.

Typically, suitable $C_6$-$C_{24}$ alkyl trimethyl quaternary ammonium salts include, but are not limited to, Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, and mixtures thereof.

Examples of suitable $C_6$-$C_{24}$ dialkyl dimethyl quaternary ammonium salts include, but are not limited to, Benzalkonium chloride, benzyl-$C_{10-16}$-alkyldimethylammonium chloride, benzyl-$C_{12-14}$-alkyldimethylammonium chloride and mixtures thereof.

Examples of suitable $C_6$-$C_{24}$ dialkyl dimethyl quaternary ammonium salts include, but are not limited to, Didecyldimonium chloride, Dilauryldimonium chloride, Distearyldimonium chloride, and mixtures thereof.

Examples of suitable esterquats include, but are not limited to, Behenoyl PG-Trimonium Chloride, Dioleoylethyl Hydroxyethylmonium Methosulfate, and mixtures thereof.

In an embodiment, the at least one cationic surfactant (b) is selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate and mixtures thereof.

In an embodiment, the at least one cationic surfactant (b) is selected from Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate and mixtures thereof.

In an embodiment, the at least one cationic surfactant (b) is selected from Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Didecyldimonium chloride, Dilauryldimonium chloride, Distearyldimonium chloride, Behenoyl PG-Trimonium Chloride, Dioleoylethyl Hydroxyethylmonium Methosulfate and mixtures thereof.

In an embodiment, the at least one cationic surfactant (b) is selected from Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Didecyldimonium chloride, Dilauryldimonium chloride, Distearyldimonium chloride and mixtures thereof.

Typically, in the compositions for dyeing keratin fibers, the total amount of (b) the at least one cationic surfactant is in the range of about 0.1 to about 15 wt. %, or about 0.15 to about 10 wt. %, or about 0.2 to about 5 wt. %, based on the total weight of the composition.

The Alkoxylated $C_6$-$C_{24}$ Fatty Alcohol

As indicated above, the composition for dyeing keratin fibers may comprise (c) at least one alkoxylated $C_6$-$C_{24}$ fatty alcohol. The term "alkoxylated $C_6$-$C_{24}$ fatty alcohol" as used herein refers to ethoxylated or propoxylated $C_6$-$C_{24}$ fatty alcohols.

Ethoxylated alcohols (also called polyethyleneglycol ethers or PEG ethers) are producted from the reaction of fatty alcohols with ethylene oxide (EO).

Typically, the average ethoxylation degree in the ethoxylated $C_6$-$C_{24}$ fatty alcohols is about 1 to 50 ethylene oxide units, or about 2 to about 30 ethylene oxide units.

Propoxylated alcohols (also called polypropyleneglycol ethers or PPG ethers) are producted from the reaction of fatty alcohols with propylene oxide (PO).

Typically, the average propoxylation degree in the propoxylated $C_6$-$C_{24}$ fatty alcohols is about 1 to 50 propylene oxide units, or about 2 to about 30 propylene oxide units.

Examples of suitable alkoxylated $C_6$-$C_{24}$ fatty alcohols include, but are not limited to, ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof.

In an embodiment, suitable alkoxylated $C_6$-$C_{24}$ fatty alcohols include, but are not limited to, ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof; in particular those having an average ethoxylation degree in the range of about 2 to about 30, or about 5 to about 25 ethylene oxide units.

Non-limiting examples of alkoxylated $C_6$-$C_{24}$ fatty alcohols that may be used according to the present disclosure, include the adducts of ethylene oxide, in particular those containing from 2 to 50 ethylene oxide units, with cetyl alcohol, stearyl alcohol, cetearyl alcohol, isostearyl alcohol, octyldodecanol, 2-ethylhexanoyl alcohol, oleyl alcohol, and mixtures thereof, such as Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof.

In an embodiment, the alkoxylated $C_6$-$C_{24}$ fatty alcohols are selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, Isoteareth-20, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, and mixtures thereof.

Typically, in the composition for dyeing keratin fibers, the total amount of (c) the at least one alkoxylated $C_6$-$C_{24}$ fatty alcohol is in the range of about 0.1 to about 15 wt. %, or about 0.3 to about 10 wt. %, or about 0.5 to about 5 wt. %, based on the total weight of the composition.

The $C_6$-$C_{24}$ Fatty Alcohol

As indicated above, the composition for dyeing keratin fibers may comprise (d) at least one $C_6$-$C_{24}$ fatty alcohol. Fatty alcohols include, but are not limited to $C_6$-$C_{24}$ fatty alcohols from vegetable fats and oils and include cotton, safflower, coconut, rapeseed, linseed, palm, palm kernel, sunflower, olein, olive, olive pomace, castor oil, soy, tall oil, etc, possibly totally or partially hydrogenated, as well as purified or synthetic fatty alcohols such as caproyl alcohol, capryl alcohol, capric alcohol, lauryl alcohol, myristyl alcohol, palmytil (cetyl) alcohol, palmitoyl alcohol, stearyl alcohol, isostearyl alcohol, 2-octyldodecanol, 2-ethylhexanoyl alcohol, oleyl alcohol, ricinoleyl alcohol, elaidyl alcohol, petroselinic alcohol, linoleyl alcohol, linolenyl alcohol, arachidyl alcohol, gadoleyl alcohol, behenyl alcohol and erucyl alcohol, or technical grade mixtures.

Examples of suitable $C_6$-$C_{24}$ fatty alcohols include, but are not limited to, lauryl alcohol, myristyl alcohol, palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof, in particular palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof.

Typically, in the composition for dyeing keratin fibers, the total amount of (d) the at least one $C_6$-$C_{24}$ fatty alcohol is in the range of about 0.1 to about 25 wt. %, or about 1 to about 20 wt. %, or about 3 to about 15 wt. %, based on the total weight of the composition.

The Oxidation Dye

As indicated above, the composition for dyeing keratin fibers may comprise (e) at least one oxidation dye. The oxidation dyes are generally chosen from one or more oxidation bases (e1) optionally combined with one or more couplers (e2).

Examples of suitable oxidation bases (e1) include, but are not limited to, p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)-1H-pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof.

Examples of suitable couplers (e2) include, but are not limited to, 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}-amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5- dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof.

Typically, in the composition for dyeing keratin fibers, the total amount of (e) oxidation dyes (including oxidation bases (e1) and couplers (e2)) is in the range of about 0.001 to about 10 wt. %, or about 0.01 to about 7.5 wt. %, or about 0.1 to about 6.5 wt. %, based on the total weight of the composition.

Ammonia

As indicated above, the composition for dyeing keratin fibers may comprise (f) ammonia. Ammonia ($NH_3$) is customarily employed in the form of its aqueous solution, in which it is present in the form of ammonium hydroxide ($NH_3OH$). Aqueous ammonia solutions include ammonia ($NH_3$) often in concentrations in the range of about 10 wt. % to about 32 wt. %.

Because ammonia is used primarily as an alkalizing agent, its use amounts depend on the pH that the ready-to-use oxidation coloring agent is to have. The skilled artisan knows that the pH of the composition for dyeing keratin fibers also increases with an increasing ammonia amount. When the composition for dyeing keratin fibers and the hydrogen peroxide composition are mixed, the ammonia content thus also determines the pH of the ready-to-use composition.

Dyeing processes on keratin fibers typically take place in an alkaline environment. To treat keratin fibers and the skin as well as gently as possible, setting a too high pH is not desirable, however. It is preferred, therefore, that the amount of ammonia used is selected so that the pH of the ready-to-use composition is between about 7 and about 11, particularly between about 8 and about 10.5, depending on other acids, buffers, or other alkalizing agents present in the ready-to-use composition. The pH values within the meaning of the present disclosure are pH values measured at a temperature of 25° C.

In an embodiment, in the composition for dyeing keratin fibers, the total amount of (f) ammonia is in the range of about 0.1 to about 10 wt. %, or about 0.2 to about 7.5 wt. %, or about 0.3 to about 4.5 wt. %, or about 0.4 to about 3.0 wt. %, or about 0.5 to about 2.8 wt. % based on the total weight of the composition.

Typically, in the composition for dyeing keratin fibers, the total amount of (f) ammonia is in the range of about 0.1 to about 10 wt. %, or about 0.3 to about 4.5 wt. %, or about 0.4 to about 3.0 wt. %, or about 0.5 to about 2.8 wt. % based on the total weight of the composition.

The Compositions for Dyeing Keratin Fibers

Typically, the composition for dyeing keratin fibers does not comprise, based on the total weight of the composition, more than 2 wt. %, or more than 1 wt. %, or more than 0.5 wt. %, or more than 0.2 w %, or more than 0.01 wt. % of alkanolamines, $C_1$-$C_4$ alkyl alkanolamines, or any fatty acid salt thereof, or mixtures thereof.

Typically, the alkanolamines and the $C_1$-$C_4$ alkyl alkanolamines are selected from monoethanolamine, diethanolamine, triethanolamine, isopropanolamine, 2-amino-2-methyl-1-propanol (AMP), 2-dimethylamino-2-methyl-1-propanol (DMAMP), tris(hydroxymethyl)aminomethane (tromethamine), N,N-diethylethanolamine (DEEA), N,N-dimethylethanolamine (DMEA), N-methyldiethanolamine (MDEA), N-methylethanolamine (NMEA), or any fatty acid salt thereof, or mixtures thereof.

Examples of fatty acids that can totally or partially neutralize the alkanolamines and the $C_1$-$C_4$ alkyl alkanolamines are selected from caproic acid, caprylic acid, capric acid, lauric acid, myristic acid, palmitic acid (cetylic acid), palmitoleic acid, stearic acid, isostearic acid, 2-ethylhexanoic acid, oleic acid, ricinoleic acid, elaidic acid, petroselinic acid, linoleic acid, linolenic acid, arachidic acid, gadoleic acid, behenic acid and erucic acid, or mixtures thereof.

In an embodiment, the composition for dyeing keratin fibers comprise, in a cosmetically acceptable medium, based on the total weight of the composition:

a) at least one anionic surfactant;
b) at least one cationic surfactant;
c) at least one alkoxylated $C_6$-$C_{24}$ fatty alcohol;
d) at least one $C_6$-$C_{24}$ fatty alcohol;
e) at least one oxidation dye;
f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In an embodiment, the composition for dyeing keratin fibers comprise, in a cosmetically acceptable medium, based on the total weight of the composition:

a) at least one anionic surfactant;
b) at least one cationic surfactant;
c) at least one alkoxylated $C_6$-$C_{24}$ fatty alcohol;
d) at least one $C_6$-$C_{24}$ fatty alcohol;
e) at least one oxidation dye;
f) about 0.1-10 wt. % of ammonia, wherein the composition does not comprise more than 0.2 wt. % of alkanolamines, $C_1$-$C_4$ alkyl alkanolamines, or any fatty acid salt thereof, or mixtures thereof.

In an embodiment, the composition for dyeing keratin fibers comprise, in a cosmetically acceptable medium, based on the total weight of the composition:

a) at least one anionic surfactant;
b) at least one cationic surfactant;
c) at least one alkoxylated $C_6$-$C_{24}$ fatty alcohol;
d) at least one $C_6$-$C_{24}$ fatty alcohol;
e) about 0.001-10 wt. % of at least one oxidation dye;
f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In an embodiment, the composition for dyeing keratin fibers comprise, in a cosmetically acceptable medium, based on the total weight of the composition:

a) at least one anionic surfactant;
b) at least one cationic surfactant;
c) at least one alkoxylated $C_6$-$C_{24}$ fatty alcohol;
d) at least one $C_6$-$C_{24}$ fatty alcohol;
e) about 0.001-10 wt. % of at least one oxidation dye;
f) about 0.2-7.5 wt. % of ammonia, wherein the composition does not comprise more than 0.2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) at least one alkoxylated $C_6$-$C_{24}$ fatty alcohol;
d) at least one $C_6$-$C_{24}$ fatty alcohol;
e) at least one oxidation dye;
f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) at least one alkoxylated $C_6$-$C_{24}$ fatty alcohol;
d) at least one $C_6$-$C_{24}$ fatty alcohol;
e) about 0.001-10 wt. % of at least one oxidation dye;
f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;
d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;
e) at least one oxidation dye;
f) about 0.1-10 wt. % of ammonia,
wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;
d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;
e) about 0.001-10 wt. % of at least one oxidation dye;
f) about 0.2-7.5 wt. % of ammonia,
wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;
d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;
e) about 0.001-10 wt. % of at least one oxidation dye;
f) about 0.4-3.0 wt. % of ammonia,
wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol;

d) at least one $C_6$-$C_{24}$ fatty alcohol;

e) about 0.001-10 wt. % of at least one oxidation dye;

f) about 0.4-3.0 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol;

d) at least one $C_6$-$C_{24}$ fatty alcohol;

e) at least one oxidation dye;

f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol;

d) at least one $C_6$-$C_{24}$ fatty alcohol;

e) at least one oxidation dye;

f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.001-10 wt. % of at least one oxidation dye;

f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium C14-C16 Olefin Sulfonate, and mixtures thereof;

b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein the compositions do not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.001-10 wt. % of at least one oxidation dye;

f) about 0.2-7.5 wt. % of ammonia, wherein the compositions do not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.001-10 wt. % of at least one oxidation dye;

f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) 0.001-10 wt. % of at least one oxidation dye;

f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, Isoteareth-20, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) 0.001-10 wt. % of at least one oxidation dye;

f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) at least one cationic surfactant selected from Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Didecyldimonium chloride, Dilauryldimonium chloride, Distearyldimonium chloride and mixtures thereof, and mixtures thereof;

c) at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) 0.001-10 wt. % of at least one oxidation dye;

f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In an embodiment, the composition for dyeing keratin fibers comprises, in a cosmetically acceptable medium, based on the total weight of the composition:

a) about 0.1-25 wt. % of at least one anionic surfactant;

b) about 0.1-15 wt. % of at least one cationic surfactant;

c) about 0.1-15 wt. % of at least one alkoxylated $C_6$-$C_{24}$ fatty alcohol;

d) about 0.1-25 wt. % of at least one $C_6$-$C_{24}$ fatty alcohol;

e) about 0.001-10 wt. % of at least one oxidation dye;

f) about 0.1-10 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.3-15 wt. % of at least one anionic surfactant;

b) about 0.15-10 wt. % of at least one cationic surfactant;

c) about 0.3-10 wt. % of at least one alkoxylated $C_6$-$C_{24}$ fatty alcohol;

d) about 1-20 wt. % of at least one $C_6$-$C_{24}$ fatty alcohol;

e) about 0.01-7.5 wt. % of at least one oxidation dye;

f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.5-10 wt. % of at least one anionic surfactant;
b) about 0.2-5 wt. % of at least one cationic surfactant;
c) about 0.5-5 wt. % of at least one alkoxylated $C_6$-$C_{24}$ fatty alcohol;
d) about 3-15 wt. % of at least one $C_6$-$C_{24}$ fatty alcohol;
e) about 0.1-6.5 wt. % of at least one oxidation dye;
f) about 0.4-3.0 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) about 0.3-15 wt. % of at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) about 0.15-10 wt. % of at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) about 0.3-10 wt. % of at least one alkoxylated $C_6$-$C_{24}$ fatty alcohol;
d) about 1-20 wt. % of at least one $C_6$-$C_{24}$ fatty alcohol;
e) about 0.01-7.5 wt. % of at least one oxidation dye;
f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) about 0.3-15 wt. % of at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;
b) about 0.15-10 wt. % of at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;
c) about 0.3-10 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;
d) about 1-20 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;
e) about 0.01-7.5 wt. % of at least one oxidation dye;
f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) about 0.3-15 wt. % of at least one anionic surfactant selected from alkyl ether carboxylates, alkyl ether sulfates, olefin sulfonates, and mixtures thereof;
b) about 0.15-10 wt. % of at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;
c) about 0.3-10 wt. % of at least one alkoxylated $C_6$-$C_{24}$ fatty alcohol;
d) about 1-20 wt. % of at least one $C_6$-$C_{24}$ fatty alcohol;
e) about 0.01-7.5 wt. % of at least one oxidation dye;
f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) about 0.5-10 wt. % of at least one anionic surfactant selected from alkyl ether carboxylates, alkyl ether sulfates, olefin sulfonates, and mixtures thereof;
b) about 0.2-5 wt. % of at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;
c) about 0.5-5 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;
d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;
e) about 0.1-6.5 wt. % of at least one oxidation dye;
f) about 0.4-3.0 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:
a) about 0.5-10 wt. % of at least one anionic surfactant selected from alkyl ether carboxylates, alkyl ether sulfates, olefin sulfonates, and mixtures thereof;
b) about 0.2-5 wt. % of at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;
c) about 0.5-5 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.5-10 wt. % of at least one anionic surfactant selected from alkyl ether carboxylates, alkyl ether sulfates, olefin sulfonates, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, Isoteareth-20, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.2-7.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, Isoteareth-20, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.3-4.5 wt. % of ammonia, wherein the composition does not comprise more than 2 wt. % of alkanolamines, $C_1$-$C_4$ alkyl alkanolamines, or any fatty acid salt thereof, or mixtures thereof.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein the composition does not comprise more than 2 wt. % of alkanolamines, $C_1$-$C_4$ alkyl alkanolamines, or any fatty acid salt thereof, or mixtures thereof.

In an embodiment, the composition for dyeing keratin fibers comprises, in a cosmetically acceptable medium, based on the total weight of the composition:

a) at least one anionic surfactant;

b) at least one cationic surfactant;

c) at least one alkoxylated $C_6$-$C_{24}$ fatty alcohol;

d) at least one $C_6$-$C_{24}$ fatty alcohol;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;

c) at least one alkoxylated $C_6$-$C_{24}$ fatty alcohol;

d) at least one $C_6$-$C_{24}$ fatty alcohol;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol;

d) at least one $C_6$-$C_{24}$ fatty alcohol;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) at least one anionic surfactant selected from alkyl ether carboxylates, alkyl ether sulfates, olefin sulfonates, and mixtures thereof;

b) at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition: a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium C14-C16 Olefin Sulfonate, and mixtures thereof; b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) at least one oxidation dye;

f) about 0.3-4.5 wt. % of ammonia, wherein ammonia is the only alkalizing agent present in the composition.

In an embodiment, the composition for dyeing keratin fibers comprises, in a cosmetically acceptable medium, based on the total weight of the composition:

a) about 0.1-25 wt. % of at least one anionic surfactant;

b) about 0.1-15 wt. % of at least one cationic surfactant;

c) about 0.1-15 wt. % of at least one alkoxylated $C_6$-$C_{24}$ fatty alcohol;

d) about 0.1-25 wt. % of at least one $C_6$-$C_{24}$ fatty alcohol;

e) about 0.001-10 wt. % of at least one oxidation dye;

f) about 0.1-10 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.3-15 wt. % of at least one anionic surfactant;

b) about 0.15-10 wt. % of at least one cationic surfactant;

c) about 0.3-10 wt. % of at least one alkoxylated $C_6$-$C_{24}$ fatty alcohol;

d) about 1-20 wt. % of at least one $C_6$-$C_{24}$ fatty alcohol;

e) about 0.01-7.5 wt. % of at least one oxidation dye;

f) about 0.3-4.5 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant;

b) about 0.2-5 wt. % of at least one cationic surfactant;

c) about 0.5-5 wt. % of at least one alkoxylated $C_6$-$C_{24}$ fatty alcohol;

d) about 3-15 wt. % of at least one $C_6$-$C_{24}$ fatty alcohol;

e) about 0.1-6.5 wt. % of at least one oxidation dye;

f) about 0.4-3.0 wt. % of ammonia, wherein ammonia is the only alkalizing agent present in the composition.

In another embodiment, the composition for dyeing keratin fibers comprises, in a cosmetically acceptable medium, based on the total weight of the compositions:

a) about 0.3-15 wt. % of at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) about 0.15-10 wt. % of at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;

c) about 0.3-10 wt. % of at least one alkoxylated $C_6$-$C_{24}$ fatty alcohol;

d) about 1-20 wt. % of at least one $C_6$-$C_{24}$ fatty alcohol;

e) about 0.01-7.5 wt. % of at least one oxidation dye;

f) about 0.3-4.5 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.3-15 wt. % of at least one anionic surfactant selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) about 0.2-10 wt. % of at least one cationic surfactant selected from alkylimidazolines, tetra alkyl(-aryl) quaternary ammonium salts (quats), heterocyclic ammonium salts, quaternized alkyl polyglycosides, quaternized derivatives of polyalkanolamine esters (esterquats), and mixtures thereof;

c) about 0.3-10 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) about 1-20 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.01-7.5 wt. % of at least one oxidation dye;

f) about 0.3-4.5 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.3-15 wt. % of at least one anionic surfactant selected from alkyl ether carboxylates, alkyl ether sulfates, olefin sulfonates, and mixtures thereof;

b) about 0.15-10 wt. % of at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) about 0.3-10 wt. % of at least one alkoxylated $C_6$-$C_{24}$ fatty alcohol;

d) about 1-20 wt. % of at least one $C_6$-$C_{24}$ fatty alcohol;

e) about 0.01-7.5 wt. % of at least one oxidation dye;

f) about 0.3-4.5 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant selected from alkyl ether carboxylates, alkyl ether sulfates, olefin sulfonates, and mixtures thereof;

b) about 0.2-5 wt. % of at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) about 0.5-5 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant selected from alkyl ether carboxylates, alkyl ether sulfates, olefin sulfonates, and mixtures thereof;

b) about 0.2-5 wt. % of at least one cationic surfactant selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) about 0.5-5 wt. % of at least one alkoxylated $C_6$-$C_{24}$ fatty alcohol selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Soytrimonium chloride, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-4, Ceteth-5, Ceteth-6, Ceteth-10, Ceteth-12, Ceteth-14, Ceteth-15, Ceteth-16, Ceteth-20, Ceteth-24, Ceteth-25, Ceteth-30, Ceteth-45, Ceteareth-4, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Steareth-5, Steareth-8, Steareth-14, Steareth-16, Steareth-21, Steareth-25, Steareth-27, Steareth-30, Steareth-40, Steareth-50, Isosteareth-2, Isoteareth-20, Oleth-2, Oleth-3, Oleth-4, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, Oleth-30, Oleth-40, Oleth-44, Oleth-50, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth- 20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, Isoteareth-20, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.2-7.5 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25, Isoteareth-20, Oleth-5, Oleth-6, Oleth-7, Oleth-8, Oleth-9, Oleth-10, Oleth-11, Oleth-12, Oleth-15, Oleth-16, Oleth-20, Oleth-23, Oleth-25, and mixtures thereof;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.3-4.5 wt. % of ammonia, wherein ammonia is the only alkalizing agent present in the composition.

In another embodiment, the composition for dyeing keratin fibers comprises, in a cosmetically acceptable medium, based on the total weight of the composition:

a) about 0.5-10 wt. % of at least one anionic surfactant selected from Potassium Laureth-4 Carboxylate, Sodium Laureth-4 Carboxylate, Sodium Laureth-5 Carboxylate, Sodium Laureth-6 Carboxylate, Sodium Laureth-11 Carboxylate, Ammonium Laureth Sulfate, Monoethanolamine (MEA)-Laureth Sulfate, Monoisopropanolamine (MIPA)-Laureth Sulfate, Sodium Laureth Sulfate, Triethanolamine (TEA)-Laureth Sulfate, Sodium $C_{14}$-$C_{16}$ Olefin Sulfonate, and mixtures thereof;

b) about 0.2-5 wt. % of at least one cationic surfactant selected from Laurtrimonium bromide, Laurtrimonium chloride, Myrtrimonium bromide, Myrtrimonium chloride, Cetrimonium bromide, Cetrimonium chloride, Cetrimonium methosulfate, Steartrimonium bromide, Steartrimonium chloride, Steartrimonium methosulfate, Behentrimonium bromide, Behentrimonium chloride, Behentrimonium methosulfate, Ceteartrimonium chloride, Cocotrimonium chloride, Cocotrimonium methosulfate, Octyl dodecyl trimethyl ammonium chloride, Dodecyl hexadecyl trimethyl ammonium bromide, Dodecyl hexadecyl trimethyl ammonium chloride, Benzalkonium chloride, benzyl-$C_{10-16}$-alkyldimethylammonium chloride, benzyl-$C_{12-14}$-alkyldimethylammonium chloride, Didecyldimonium chloride, Dilauryldimonium chloride, Distearyldimonium chloride, Behenoyl PG-Trimonium Chloride, Dioleoylethyl Hydroxyethylmonium Methosulfate, and mixtures thereof;

c) about 0.5-5 wt. % of at least one alkoxylated $C_6$-$C_{24}$ fatty alcohol selected from Ceteth-5, Ceteth-6, Ceteth-10, Ceteth-12, Ceteth-14, Ceteth-15, Ceteth-16, Ceteth-20, Ceteth-24, Ceteth-25, Ceteareth-5, Ceteareth-6, Ceteareth-7, Ceteareth-8, Ceteareth-9, Ceteareth-10, Ceteareth-11, Ceteareth-12, Ceteareth-13, Ceteareth-14, Ceteareth-15, Ceteareth-16, Ceteareth-17, Ceteareth-18, Ceteareth-20, Ceteareth-22, Ceteareth-23, Ceteareth-24, Ceteareth-25, Steareth-5, Steareth-8, Steareth-14, Steareth-16, Steareth-21, Steareth-25;

d) about 3-15 wt. % of at least one $C_6$-$C_{24}$ fatty alcohol selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) about 0.1-6.5 wt. % of at least one oxidation dye;

f) about 0.4-3.0 wt. % of ammonia, wherein ammonia is the only alkalizing agent present in the composition.

In an embodiment, in the compositions for dyeing keratin fibers the weight ratio between (a) the at least one anionic surfactant and (b) the at least one cationic surfactant ranges from about 30:1 to about 1:1, or from about 15:1 to about 1:1, or from about 10:1 to about 2:1.

In another embodiment, in the compositions for dyeing keratin fibers the weight ratio between (d) the at least one $C_6$-$C_{24}$ fatty alcohol and (c) the at least one alkoxylated $C_6$-$C_{24}$ fatty alcohol ranges from about 40:1 to about 1:1, or from about 30:1 to about 5:1, or from about 20:1 to about 7:1.

Other Ingredients

The compositions for dyeing keratin fibers may contain a variety of other ingredients to enhance the beneficial properties of the dyeing compositions, as further described herein.

1. Thickening Agents

In an embodiment, the compositions for dyeing keratin fibers may contain one or more agents that will provide a thickening, or viscosity increasing, effect to the dyeing compositions. Suitable thickening agents include, but are not limited to, anionic, synthetic polymers, cationic synthetic polymers, naturally occurring thickeners, such as nonionic guar gums, scleroglucan gums or xanthan gums, gum arabic, gum ghatti, karaya gum, tragacanth gum, carrageenan gum, agar-agar, locust bean gum, pectins, alginates, starch fractions, and derivatives such as amylose, amylopectin, and dextrins, as well as cellulose derivatives such as, for example, methylcellulose, carboxyalkylcelluloses, and hydroxyalkylcelluloses, nonionic, fully synthetic polymers, such as polyvinyl alcohol or polyvinylpyrrolidinone; as well as inorganic thickeners, in particular phyllosilicates such as, for example, bentonite, in particular smectites, such as montmorillonite or hectorite. Suggested ranges are from about 0.001-20 wt. %, or about 0.005-15 wt. %, or about 0.01-12 wt. %, based on the total weight of the composition.

2. Preservatives

In an embodiment, the compositions for dyeing keratin fibers may contain one or more preservatives. Suitable preservatives include, but are not limited to, methyl, ethyl, and propyl paraben, hydantoins, and the like. Suggested ranges are about 0.0001-8 wt. %, or about 0.0005-7 wt. %, or about 0.001-5 wt. %, based on the total weight of the composition.

3. Chelating Agents

The dyeing compositions may also contain about 0.0001-5 wt. %, or 0.0005-3 wt. %, or 0.001-2 wt. %, based on the total weight of the composition, of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include, but are not limited to, sodium citrate; nitrogen-containing polycarboxylic acids, particularly Ethylenediaminetetraacetate (EDTA), and calcium, sodium, potassium or triethanolamine derivatives thereof, Hydroxyethyl Ethylenediamine Triacetic Acid (HEDTA), Ethylenediamine-N,N'-disuccinic acid (EDDS); and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

4. pH Adjusters

It may also be desirable to add small amounts of acids or buffering systems to adjust the pH of the dyeing compositions to the desired pH range of 7.1 to 11. Suitable acids include hydrochloric acid, phosphoric acid, citric acid, and the like. Suggested ranges of pH adjusters are from about 0.00001-8 wt. %, or about 0.00005-6 wt. %, or about 0 0001-5 wt. %, based on the total weight of the composition.

5. Reducing Agents

The dyeing compositions may also contain reducing agents to retard the reaction between oxidation bases and couplers and to prevent the initiation of the reaction in the packaging during the storage time. Sodium metabisulfite (sodium pyrosulfite) or sodium sulfite are typically used for this purpose.

6. Antioxidants

The dyeing compositions may also contain antioxidants to avoid the reaction beginning before the addition of the oxidizing agent (e.g., hydrogen peroxide).

Water-soluble antioxidants such as erythorbic acid or oil-soluble antioxidants such as T-butylquinone are typically used.

7. Opacifiers

The dyeing compositions may also contain opacifiers. Suitable opacifiers include, but are not limited to, titanium dioxide (TiO2), latex, styrene/PVP, styrene/acrylamide copolymers, and mixtures thereof.

8. Pigments

The dyeing compositions may also contain inorganic pigments. Suitable inorganic pigments include, but are not limited to, those having a color index number as listed in the CTFA dictionary, 10th edition, 2004, hereby incorporated by reference.

9. Direct Dyes

The dyeing compositions may also contain direct dyes. Direct dye, also called substantive dye, is a dye that adheres to its substrate, by non-ionic forces, e.g., without help from other chemicals. For purposes of this disclosure dyes include direct dyes selected from anionic, cationic and non-ionic nitro dyes.

Examples of anionic direct dyes include, but are not limited to, Bromophenol Blue, Tetrabromophenol Blue, Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 5, FD&C Yellow No. 6, FD&C Blue 1, Food Black 1, Food Black 2, Disperse Black 9 and Disperse Violet 1 and their alkali metal salts such as sodium, potassium.

Examples of cationic dyes include, but are not limited to, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12, Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 31.

Examples of non-ionic nitro dyes (HC dyes) include, but are not limited to, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 15, Blue No. 16, HC Blue No. 18, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 14, HC Red No. 18, HC Red No. 54, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

10. Fragrance or Perfumes

For purposes of this disclosure, the term "fragrance" as used herein refers to any substance, natural or synthetic, used to impart an odour to a product.

For purposes of this disclosure, the term "perfume" as used herein refers to any mixture of fragrant essential oils and aroma compounds, fixatives, and solvents used to give the human body, objects, and living spaces a lasting and pleasant smell.

11. Nonionic Surfactants Different from the $C_6$-$C_{24}$ Fatty Alcohols

Non-limiting examples of nonionic surfactants different from the $C_6$-$C_{24}$ fatty alcohols in the context of the present disclosure include, but are not limited to, polyethoxylated or polypropoxylated fatty acids, alkylphenols, alpha-diols or alcohols having a fatty chain containing, for example, 8 to 18 carbon atoms, ethylene oxide or propylene oxide groups to range in particular from 2 to 50; copolymers of ethylene oxide and of propylene oxide, polyethoxylated fatty amides having from 2 to 30 mol of ethylene oxide; polyglycerolated fatty amides containing on average 1 to 5, or 1.5 to 4, glycerol groups; polyethoxylated fatty amines having 2 to 30 mol of ethylene oxide; oxyethylenated fatty acid esters of sorbitan having from 2 to 30 mol of ethylene oxide; fatty acid esters of sucrose; fatty acid esters of polyethylene glycol; alkylpolyglycosides; N-alkylglucamine derivatives; amine oxides such as ($C_{10}$-$C_{14}$) alkylamine oxides or N-acylaminopropylmorpholine oxides.

12. Amphoteric or Zwitterionic Surfactants

Non-limiting examples of amphoteric or zwitterionic surfactants include, but are not limited to, aliphatic secondary or tertiary amine derivatives in which the aliphatic radical is a linear or branched chain containing 8 to 18 carbon atoms and containing at least one water-soluble anionic group (for example carboxylate, sulphonate, sulphate, phosphate or phosphonate); ($C_8$-$C_{20}$) alkylbetaines, sulphobetaines, ($C_8$-$C_{20}$) alkylamido ($C_1$-$C_6$) alkylbetaines or ($C_8$-$C_{20}$) alkylamido ($C_1$-$C_6$) alkylsulphobetaines; amine derivatives, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

13. Petroleum hydrocarbons (mineral oils, paraffins and waxes)

For purposes of this disclosure petroleum hydrocarbons are represented as mineral oils, paraffins and waxes based on petroleum. Examples include, but are not limited to, hard paraffin, liquid paraffin (Liquid Petrolatum or Paraffinum Liquidum), light liquid paraffin (Light Liquid Petrolatum or Paraffinum Perliquidium), white soft paraffin (White Petrolatum), yellow soft paraffin (Yellow Petrolatum), macrocrystalline paraffin waxes (which are mixtures which consist mainly of saturated $C_{18}$-$C_{30}$ hydrocarbons and smaller amounts of iso-alkanes and cycloalkanes with a molecular weight comprised between 250 and 450 g/mol and, although they are solids at room temperature, they have low melting points, usually comprised between 40° C. and 60° C.), microcrystalline paraffin waxes (which consist of $C_{40}$-$C_{55}$ compounds which contain, in addition to normal hydrocarbons, included in the group areiso-alkanes and naphtenes with long alkyl side-chains, the iso-alkanes forming microcrystals, the microcrystalline paraffin waxes having mean molecular weights comprised between 500 and 800 g/mol, being solids at room temperature, and having melting points comprised between 60° C. and 90° C.), or mixtures thereof.

14. Vegetable Fats and Oils

For purposes of this disclosure vegetable fats and oils are linear and/or branched esters, linear or branched, saturated and/or unsaturated alkanecarboxylic acids with a chain length of 1 up to 30 carbon atoms, saturated and/or unsaturated alcohols with a chain length of 1 up to 30 carbon atoms; or linear and/or branched esters of aromatic carboxylic acids, or saturated and/or unsaturated alcohols with a chain length of 1 up to 30 carbon atoms. These oils can be selected from the group consisting of for example isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl laurate, 2-ethylhexyl palmitate, 2-ethylhexyl cocoate, 2-hexyldecyl stearate, 2-ethylhexyl isostearate, 2-octyldodecyl palmitate, cetyl palmitate, stearyl palmitate, oleyl palmitate, oleyl oleate, oleyl erucate, erucyl oleate, erucyl erucate, as well as synthetic, semisynthetic and natural mixtures esters, such as jojoba oil (a natural mixture of esters of monounsaturated monocarboxylic acids with a $C_{13}$-$C_{24}$ chain with also monounsaturated monoalcohols and with a long $C_{13}$-$C_{24}$ chain).

Other examples of vegetable fats and oils include ester oils such as sugar esters or diesters of $C_{12}$-$C_{24}$ fatty acids. The term "sugar" means compounds comprising several alcohol functions, with or without an aldehyde or ketone function, and which comprise at least 4 carbon atoms. These sugars may be monosaccharides, oligosaccharides or polysaccharides.

Non-limiting examples of sugars that may be used according to the present disclosure, include sucrose (or saccharose), glucose, galactose, ribose, fucose, maltose, fructose, mannose, arabinose, xylose and lactose, and derivatives thereof, including for example, alkyl derivatives such as methyl derivatives, for instance methylglucose. Non-limiting examples of the sugar esters of fatty acids that may be used according to this disclosure include those from the group comprising esters or mixtures of esters of sugars described above and of linear or branched, saturated or unsaturated $C_{12}$-$C_{24}$ fatty acids.

The esters may be chosen from mono-, di-, tri-, tetraesters and polyesters, and mixtures thereof. These esters may be chosen from, for example, but not limited to, oleates, laurates, palmitates, myristates, behenates, cocoates, stearates, linoleates, linolenates, caprates and arachidonates, or mixtures thereof such as oleo-palmitate, oleo-stearate and palmito-stearate mixed esters. It will be noted that the sucrose, glucose or methylglucose monoesters and diesters and for example sucrose, glucose or methylglucose mono- or dioleates, stearates, behenates, oleopalmitates, linoleates, linolenates and oleostearates, constitute sugar esters or diesters of $C_{12}$-$C_{24}$ fatty acids that are suitable in the context of the present disclosure. A particular non-limiting example that may be mentioned is methylglucose dioleate.

Other suitable oils of the type of esters of saturated alkane carboxylic acids and alcohols are fatty acid methyl esters, such as $C_6$-$C_{24}$ fatty acid methyl esters from animal and vegetable fats and oils such as cotton, safflower, coconut, rapeseed, linseed, palm, palm kernel, sunflower, olein, olive, olive pomace, castor oil, soy, tall oil, etc, possibly totally or partially hydrogenated, as well as purified or synthetic fatty acids such as caproic acid, caprylic acid, capric acid, lauric acid, myristic acid, palmitic acid (cetylic acid), palmitoleic acid, stearic acid, isostearic acid, 2-ethylhexanoic acid, oleic acid, ricinoleic acid, elaidic acid, petroselinic acid, linoleic acid, linolenic acid, arachidic acid, gadoleic acid, behenic acid and erucic acid, or mixtures thereof.

Other suitable vegetable fats and oils according to the present disclosure are fatty acid triglycerides, including for example, linear and/or branched triglycerin esters, saturated and/or unsaturated alkanecarboxylic acids with a chain length of 6 up to 24 carbon atoms, preferably of 10 up to 18 carbon atoms. The fatty acids esterifying the different positions of glycerin can be different, giving rise to a large amount of possible combinations, including positional combinations. The position of the different fatty acids in natural triglycerides is not random, but rather it depends on the origin of the fat. The most simple triglycerides are those constituted by a sole fatty acid.

Fatty acid triglycerides can be chosen, for example, from the group consisting of synthetic, semi-synthetic and natural oils, as for example avocado oil, almond oil, hazelnut oil, babassu palm oil, borage oil, peanut oil, canola oil, hemp oil, milk thistle oil, safflower oil, chufa oil, coconut oil, rapeseed oil, black cumin oil, wheat germ oil, sunflower oil, linseed oil, macadamia nut oil, corn oil, walnut oil, olive oil and its by-products such as olive pomace oil, palm oil and its fractions such as palm olein and palm stearin, evening primrose oil, rosehip oil, castor oil, rice bran oil, apricot kernel oil, cottonseed oil, pumpkinseed oil, palm kernel oil and its fractions such as palm kernel olein and palm kernel stearin, grape seed oil, sesame oil, soy oil, cocoa butter, shea butter and the like.

15. Natural Waxes

Natural waxes according to the present disclosure, include but are not limited to, candelilla wax, carnauba wax, Japan wax, esparto wax, cork wax, guaruma wax, rice wax, sugar cane wax, ouricury wax, montan wax, beeswax, shellac wax, espermaceti, wool lanolin (wax), uropygial fat wax, ceresin waxes, peat waxes, ozokerite, as well as chemically modified waxes (hard waxes) for example, montan wax esters, waxes obtained by the Fischer-Tropsch process, hydrogenated jojoba waxes and synthetic waxes.

16. Silicones

For purposes of the present disclosure silicones include, cyclic and/or linear silicones, which can be found as monomers generally characterized by structural elements such as:

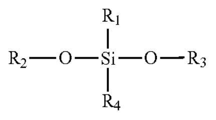

where the silicon atoms can be substituted by alkyl or aryl radicals equal or different, represented here generally by $R_1$-$R_4$ groups.

Linear silicones with siloxane units suitable according to the present disclosure are generally characterized by structural elements such as:

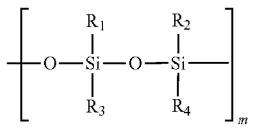

where the silicon atoms can be substituted by alkyl or aryl radicals equal or different, represented here in general by $R_1$-$R_4$ groups (meaning the number of different radicals is not necessarily limited to 4), m can take values from 2 to 200.000.

Cyclic silicones suitable according to the present disclosure are generally characterized by structural elements such as:

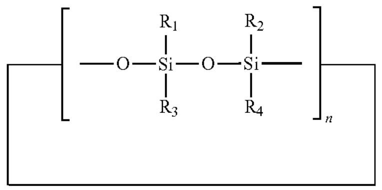

where the silicon atoms can be substituted by alkyl or aryl radicals equal or different, represented here generally by $R_1$-$R_4$ groups (meaning the number of different radicals is not necessarily limited to 4), n can take values of 3/2 to 20. Fractional values of n indicate that it may be odd numbers of siloxane groups present in the ring.

Specific examples include a cyclic methyl siloxane having the formula $[(CH_3)_2SiO]x$ in which x is 3-6, or short chain linear methyl siloxanes having the formula $((CH_3)_2SiO[(CH_3)_2SiO]_ySi(CH_3)_3$ in which y is 0-5.

Some suitable cyclic methyl siloxanes are hexamethylcyclotrisiloxanes (D3), octamethylcyclotetrasiloxane (D4), decamethylcyclopentasiloxane (D5) (cyclomethicone) and dodecamethylcyclohexasiloxane (D6).

Some suitable short linear methyl siloxane are hexamethyldisiloxane (MM), octamethyltrisiloxane (MDM), decamethyltetrasiloxane (MD2M), dodecamethylpentasiloxane (MD3M), tetradecamethylhexasiloxane (MD4M), and hexadecamethylheptasiloxane (MD5M).

Furthermore, long chain linear siloxanes such as phenyltrimethicone, bis(phenylpropyl)dimethicone, dimethicone, dimethiconol, cetyldimethicone and behenoxy dimethicone are also suitable silicones according to the present disclosure.

17. Cationic Polymers

The term "cationic polymer" as used herein refers to a macromolecule (polymer) that contains at least one monomer bearing a quaternary ammonium group.

Examples of suitable cationic polymers include, but are not limited to, those polymers known by their International Nomenclature for Cosmetic Ingredients (INCI) name as Polyquaternium. Typical examples of those are Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-42, Polyquaternium-43, Polyquaternium-44, Polyquaternium-45, Polyquaternium-46, Polyquaternium-47, Polyquaternium-48, Polyquaternium-49, Polyquaternium-50, Polyquaternium-51, Polyquaternium-52, Polyquaternium-53, Polyquaternium-54, Polyquaternium-55, Polyquaternium-56, Polyquaternium-57, Polyquaternium-58, Polyquaternium-59, Polyquaternium-60, Polyquaternium-61, Polyquaternium-62, Polyquaternium-63, Polyquaternium-64, Polyquaternium-65, Polyquaternium-66, Polyquaternium-67, Polyquaternium-68, Polyquaternium-69, Polyquaternium-70, Polyquaternium-71, Polyquaternium-72, Polyquaternium-73, Polyquaternium-74, Polyquaternium-75, Polyquaternium-76, Polyquaternium-77, Polyquaternium-78, Polyquaternium-79, Polyquaternium-80, Polyquaternium-81, Polyquaternium-82, Polyquaternium-83, Polyquaternium-84, Polyquaternium-85, Polyquaternium-86, Polyquaternium-87, Polyquaternium-88, Polyquaternium-91, Polyquaternium-92, Polyquaternium-94, Polyquaternium-95, Polyquaternium-96, Polyquaternium-98, Polyquaternium-99, Polyquaternium-100, Polyquaternium-102, Polyquaternium-104, Polyquaternium-109, Polyquaternium-110, Polyquaternium-111, Polyquaternium-112, Polyquaternium-113 and Polyquaternium-114. Other suitable cationic polymers include those known by their INCI name as Guar hydroxypropyl trimonium chloride, Polyacrylamidopropyltrimonium Chloride, Polymethacrylamidopropyltrimonium Chloride and Polymethacrylamidopropyltrimonium Methosulfate.

18. Non-Ionic Polymers

For purposes of this disclosure, non-limiting examples of non-ionic polymers include, but are not limited to:

- nonionic guar gums and modified nonionic guar gums may be for example, but are not limited to, those modified with $C_1$-$C_6$ hydroxyalkyl groups;
- biopolysaccharide gums of microbial origin such as scleroglucan gum or xanthan gum;
- gums derived from plant exudates, such as gum arabic, ghatti gum, karaya gum, tragacanth gum, carrageenan, agar and carob gum;
- pectins;
- alginates;
- starches;
- hydroxy ($C_1$-$C_6$) alkylcelluloses and carboxy ($C_1$-$C_6$) alkylcelluloses;
- celluloses modified with groups comprising at least one fatty chain; non-limiting mention may be made, for example, of hydroxyethylcelluloses modified with groups comprising at least one fatty chain, such as alkyl, arylalkyl or alkylaryl groups, or mixtures thereof, and wherein the alkyl groups are, for example, $C_8$-$C_{22}$; or those modified with polyalkylene glycol alkylphenyl ether groups;
- hydroxypropyl guars modified with groups comprising at least one $C_8$-$C_{22}$ fatty chain,
- copolymers of vinylpyrrolidone and of hydrophobic monomers comprising a fatty chain, such as vinylpyrrolidone/hexadecene copolymer or vinylpyrrolidone/eicosene copolymer;
- copolymers of $C_1$-$C_6$ alkyl acrylates or methacrylates and of amphiphilic monomers comprising at least one fatty chain;
- copolymers of hydrophilic acrylates or methacrylates and of hydrophobic monomers comprising at least one fatty chain, such as the polyethylene glycol methacrylate/lauryl methacrylate copolymer;
- polymers with an aminoplast ether skeleton comprising at least one fatty chain;
- polyurethane polyethers comprising in their chain both hydrophilic blocks, for example of polyoxyethylenated nature, and hydrophobic blocks that may be aliphatic blocks alone and/or cycloaliphatic and/or aromatic blocks.

19. Amphoteric Polymers

For purposes of this disclosure, non-limiting examples of amphoteric polymers include, but are not limited to, amphoteric polysaccharides such as Carboxymethylchitosan or N-[(2'-Hydroxy-2',3'-dicarboxy)ethyl]chitosan; Amphoteric Urethanes; Modified Potato Starch; Methacryloyl Ethyl Betaine/Acrylates Copolymer; Acrylates/Lauryl Acrylate/Stearyl Acrylate/Ethylamine Oxide Methacrylate; and Acrylic acid/(meth)acrylamidopropyl-trimethylarnmonium chloride/stearyl methacrylate terpolymer.

In a particular embodiment, the compositions for dyeing keratin fibers exhibit optical anisotropy, i.e. the compositions for dyeing keratin fibers display Malta crosses under polarized light.

The dyeing composition according to the present disclosure can suppress its offensive ammonia odor. Specifically, the dyeing composition can suppress offensive ammonia odor as stored alone (as it is) and ammonia odor which may generate when this dyeing composition is mixed with a hydrogen peroxide composition (e.g. a developer).

Although the present disclosure should not be regarded as bound to the theory discussed hereinafter, it is believed that those beneficial effects may be attributable to a particular structural arrangement of the composition, which is evident by its optical and rheological properties.

No particular limitation is imposed on the form of the compositions for dyeing keratinous fibers of the present disclosure. Examples include powder, transparent liquid, emulsion, cream, mousse, gel, paste, aerosol, and aerosol foam.

Structured fluids, such as cosmetics, typically contain particles or droplets of an immiscible fluid suspended in a carrier liquid.

Structured fluids have complex rheological behaviours. Structured fluids do not obey a simple linear relationship between applied stress and flow (Newtonian fluid behavior). Nearly all these materials have a viscosity that drops at higher rates of shear velocity resp, stress. This is the phenomenon of shear thinning which becomes progressively larger as the volume concentration of suspended particles increases. At high concentration of solid content, the low shear rate viscosity region disappears completely, the material is yielding.

Some materials show after the shear thinning region with increasing rate or stress, an increase of the viscosity, usually due to structure rearrangements as a result of the applied shear. This is referred to as flow induced shear thickening.

Viscoelasticity is the property of a material to store or dissipate mechanical energy, showing both viscous and elastic behaviors. It can be assessed through Rheometer Oscillation tests.

Typically, the compositions for dyeing keratin fibers of the present disclosure present a critical stress, measured through an Amplitude Sweep from 0.01% to 80% of Strain % (25° C.-1 Hz), in the range of 20-150 Pa, or about 25-125 Pa, measured a HR-1 Hybrid Rheometer supplied by TA Instruments.

Typically, the compositions for dyeing keratin fibers of the present disclosure present a complex viscosity in the range of 1.500-12.500 Pa·s, or in the range of about 5.000-7.000 Pa·s, measured at 0.02 Hz through a Frequency Sweep from 20 to 0.02 Hz. (25° C.-0.1% Strain %), with a HR-1 Hybrid Rheometer supplied by TA Instruments.

The term "critical stress" as used herein, refers to the Oscillation Stress (Pa) measured through an Amplitude Sweep where G" (loss modulus, Pa) is =G' (Storage modulus, Pa) (*Understanding Rheology of Structured Fluids*, T&A Instruments, AAN016)

The term "complex viscosity" (r*) as used herein refers to the frequency-dependent viscosity function determined during forced harmonic oscillation of shear stress (*Guide to Rheological Nomenclature: Measurements in Ceramic Particulate Systems*, Vincent A. Hackley and Chiara F. Ferraris, 2001).

$$\eta^* = \eta' + j\eta''$$

Where $\eta^*$ is the complex viscosity, $\eta'$ is termed the dynamic viscosity, and is equivalent to the ratio of the stress in phase with the rate of strain, $\eta''$ is referred to as the out-of-phase viscosity, and is equivalent to the ratio of the stress 90° out of phase with the rate of strain and $j=\sqrt{-1}$.

Both the critical stress and the complex viscosity serve as an indication of the rheological properties and stability of the dyeing compositions after applying mechanical stress.

The Process for Preparing a Dyeing Composition

Another embodiment of the present disclosure refers to a process for preparing a dyeing composition as defined above comprising the steps of:

i) adding (a) at least one anionic surfactant, (c) least one alkoxylated $C_6$-$C_{24}$ fatty alcohol, (d) at least one $C_6$-$C_{24}$ fatty alcohol and (e) at least one oxidation dye to a water phase at a temperature from about 50° C. to about 90° C. and under agitation;

ii) cooling the emulsion obtained in step (i) to a temperature from about 30° C. to about 50° C. and under agitation;

iii) adding (b) at least one cationic surfactant and (f) ammonia to the emulsion obtained in step (ii) under agitation.

Step (i) is a step to add (a) at least one anionic surfactant, (c) least one alkoxylated $C_6$-$C_{24}$ fatty alcohol, (d) at least one $C_6$-$C_{24}$ fatty alcohol and (e) at least one oxidation dye to a water phase. Step (i) can be carried out at a temperature from about 50° C. to about 90° C., or from about 60° C. to 80° C., under agitation.

Typically, the water phase is heated up to a temperature from about 50° C. to about 90° C., or from about 60° C. to 80° C., and then (a) at least one anionic surfactant, (c) least one alkoxylated $C_6$-$C_{24}$ fatty alcohol, (d) at least one $C_6$-$C_{24}$ fatty alcohol and (e) at least one oxidation dye are added to the water phase under agitation. The components can be added all together or one-by-one. In a particular embodiment, the least one alkoxylated $C_6$-$C_{24}$ fatty alcohol (c) and the at least one $C_6$-$C_{24}$ fatty alcohol (d) are added first under agitation to the water phase, then the at least one oxidation dye (e) is added under agitation, and then at least one anionic surfactant (a) is added subsequently added under agitation.

Step (ii) is a step to cool down the mixture emulsion obtained in (i). Step (ii) can be carried out at a temperature from about 30° C. to about 50° C.

Step (iii) is a step to add (b) at least one cationic surfactant and (f) ammonia to the emulsion obtained in step (ii) under agitation. The components can be added all together or one-by-one. In a particular embodiment, the at least one cationic surfactant (b) is added first under agitation and then (f) ammonia is added subsequently added under agitation.

Another embodiment of the present disclosure refers to a process for preparing a dyeing composition as defined above comprising the steps of:

i.a) adding (c) least one alkoxylated $C_6$-$C_{24}$ fatty alcohol, (d) at least one $C_6$-$C_{24}$ fatty alcohol and (e) at least one oxidation dye to a water phase at a temperature from about 50° C. to about 90° C. and under agitation;

i.b) adding (e) at least one oxidation dye to the emulsion obtained in step (i.a) at a temperature from about 50° C. to about 90° C. and under agitation;

i.c) adding (a) at least one anionic surfactant to the emulsion obtained in step (i.b); ii) cooling the emulsion obtained in step (i.c) to a temperature from about 30° C. to about 50° C. and under agitation;

iii.a) adding (b) at least one cationic surfactant to the emulsion obtained in step (ii) under agitation;

iii.b) adding (f) ammonia to the emulsion obtained in step (iii.a) under agitation.

Another embodiment of the present disclosure refers to a dyeing composition obtained by the process described above, in particular wherein the composition exhibits anisotropy.

The Process for the Permanent Dyeing of Keratin Fibers

Another embodiment of the present disclosure refers to a process for the permanent dyeing of keratin fibers comprising the steps of:

i) mixing, before application, a composition for dyeing keratin fibers as defined above, with a hydrogen peroxide composition, to form a ready-to-use composition;

ii) applying the ready-to-use composition obtained in step (i) to the keratin fibers for a period which is sufficient to obtain the dyeing effect;

iii) removing the ready-to-use composition from the keratin fibers by rinsing with water.

Another embodiment of the present disclosure refers to a process for the permanent dyeing of keratin fibers as described above, wherein the process is intended for reducing the difference in color between the roots and the dyed keratinous fiber (touch up), i.e. to cover gray roots or faded keratinous fibers before the next dyeing process, and/or to rejuvenate the color of the fibers.

Another embodiment of the present disclosure refers to a process for the permanent dyeing of keratin fibers as described above, wherein the keratinous fibers are dyed a reduced period of time, i.e. in less than about 15 minutes, or less than about 10 minutes, or less than about 5 minutes.

The mixing ratio of the composition for dyeing keratin fibers and the hydrogen peroxide composition (i.e. developer) may be about 1:1 to 1:3, or about 1:1 to 1:2.5.

It should be noted that the mixing ratio of the composition for dyeing keratin fibers of the disclosure and the hydrogen peroxide composition is very much dependent on the level of dyeing effect targeted. The above mentioned ratios are general and in case somewhat different mixing ratios are needed simply because of reaching higher dyeing level than usual levels, such mixing ratio should still be understood being within the scope of the present disclosure.

Typically, the hydrogen peroxide composition is in the form of an aqueous solution (aqueous hydrogen peroxide composition). The term "aqueous" means that the hydrogen peroxide composition comprises more than about 5 wt. % of water, or more than about 10 wt. % of water, or more than 20 wt. % of water.

The concentration of hydrogen peroxide may range from about 1 to 50 wt. %, or from about 2 to 40 wt. %, or from about 2 to 15 wt. %.

As a function of the desired degree of lightening, the hydrogen peroxide composition may also comprise an oxidizing agent preferably chosen from peroxygenated salts.

The aqueous hydrogen peroxide composition may further comprise those substances customarily found in oxidizing compositions such as chelating agents, such as Ethylenediaminetetraacetate (EDTA), and/or its salts. Typically, the pH of this aqueous hydrogen peroxide composition is in the range of about 2 to about 7, or in the range of about 2.5 to about 6, or in the range of about 2.5 to about 5.

Typically, the hydrogen peroxide composition is in various forms, for instance a solution, an emulsion or a gel.

Next, the mixture of the composition according to the present and the hydrogen peroxide composition is applied onto keratin fibers such as hair, and washed out after appropriate processing time. As a result, the keratin fibers such as hair can be colored.

Typically, the pH of the ready-to-use composition, mixture of the composition for dyeing keratin fibers of the disclosure and the hydrogen peroxide composition, is in the range of about 8 to about 12, or in the range of about 9 to about 11.

The Multi-Compartment Device

Another embodiment of the present disclosure refers to a multi-compartment device for dyeing keratin fibers comprising at least two compartments packaged separate from one another, wherein one compartment comprises a composition for dyeing keratin fibers as defined above; and a second compartment comprises a hydrogen peroxide composition.

Typically, the multi-compartment device for dyeing keratin fibers is a multi-component packaging unit (kit-of-parts) including at least two compartments packaged separate from one another, wherein one compartment comprises a composition for dyeing keratin fibers as defined above; and a second compartment comprises a hydrogen peroxide composition.

Another embodiment of the present disclosure refers to a composition for dyeing keratin fibers as defined above, wherein the composition is contained in one compartment of a multi-compartment device, and wherein a second compartment comprises a hydrogen peroxide composition.

The composition for dyeing keratin fibers as defined above and the hydrogen peroxide composition, packaged separate from one another, can be provided in separate containers, which are located together in an outer package (i.e. a cardboard box or a carton). Alternatively, the composition for dyeing keratin fibers as defined above and the hydrogen peroxide composition can be provided in two separate containers, which are purchased separately from one another and are mixed together before use.

The composition for dyeing keratin fibers as defined above and the hydrogen peroxide composition, packaged separate from one another, can also be provided in a single multi-chamber container (dispenser) such as an aerosol can.

The following examples are given in order to provide a person skilled in the art with a sufficiently clear and complete explanation of the present disclosure, but should not be considered as limiting of the essential aspects of its subject, as set out in the preceding portions of this description.

EXAMPLES

1. Preparation of the Dyeing Compositions

The compositions of Table 1 were prepared. CE1-CE3 represent comparative experiments.

TABLE 1

Compositions for dyeing keratin fibers (wt. % based on the total weight of the composition).

| Ingredients | C1 | C2 | C3 | CE1 | CE2 | CE3 |
|---|---|---|---|---|---|---|
| Sodium Laureth Sulfate | 0.7 | | 0.7 | 0.7 | — | — |
| Sodium C14-C16 Olefin sulfonate | — | 0.7 | — | — | — | — |
| Cocamidopropyl betaine | — | — | — | — | — | 1.2 |
| Cetrimonium Chloride | 0.25 | 0.25 | — | — | 0.25 | — |
| Dicetyldimonium chloride | — | — | 0.25 | — | — | — |
| Ceteareth-20 | 0.6 | 0.6 | 0.6 | 0.6 | 0.6 | — |
| Ceteareth-50 | — | — | — | — | — | 4.5 |
| Lauryl alcohol | — | — | — | — | — | 1.3 |
| Myristyl alcohol | — | — | — | — | — | 3.7 |
| Cetearyl alcohol | 7.3 | 7.3 | 7.3 | 7.3 | 7.3 | 6.0 |
| Stearyl alcohol | — | — | — | — | — | 12.0 |
| Behenyl alcohol | 1.0 | 1.0 | 1.0 | 1.0 | 1.0 | — |
| Ammonia (as ammonium hydroxide) | 2.0 | 2.0 | 2.0 | 2.0 | 2.0 | 2.0 |
| Oxidation dyes to provide dark Auburn shade | 2.6 | 2.6 | 2.6 | 2.6 | 2.6 | 2.6 |
| Aqua (Water) (Eau) and butylene glycol | 84.4 | 84.4 | 84.4 | 84.4 | 84.4 | 64.4 |
| Perfume, preservatives, antioxidants, reducing agents, chelating agents | Up to 100 | Up to 100 | Up to 100 | Up to 100 | Up to 100 | Up to 100 |

The compositions were prepared by placing about 70% of the water in a main kettle having a homogeneizer mill attached and heating to about 70-80° C. While maintained the temperature and agitation, a chelating agent (tetrasodium EDTA), Ceteareth-20, Cetearyl alcohol and Behenyl alcohol were added to water. The mixture was further milled for about 15 minutes.

In a separate kettle, the remaining about 30% of water, butylene glycol, a reducing agent and an antioxidant were mixed and heated to about 70-80° C. The dyes were then added to the mixture. Then this mixture was added to the previous mixture of other ingredients in the main kettle. The resulting mixture was further milled for about 15 minutes.

The anionic surfactant (when present) was added to the mixture while maintained the temperature and agitation. The resulting mixture was further milled for about 15 minutes.

The mixture was cooled to about 40-50° C. The cationic surfactant (when present) was added to the mixture while maintained the temperature and agitation. The resulting mixture was further milled for about 5 minutes While maintained the temperature and agitation, ammonia (in the form of ammonia hydroxide) was added to the mixture. The resulting mixture was further milled for about 5 minutes.

The mixture was cooled to about 30-40° C. Perfume was added while maintained the temperature and agitation. The resulting mixture was further milled for about 15 minutes.

The mixture was finally cooled to 25° C.

CE2 was discarded because no stable emulsion was obtained but two separate phases.

2. Preparation of the Ready-to-Use Compositions

Each dyeing composition (C1, C2, C3, CE1 and CE3) were mixed in a non-metallic bowl at a ratio 1:1 by weight with a commercially available 6 wt. % (20 Vol) aqueous hydrogen peroxide composition to obtain ready-to-use compositions.

3. Dyeing Evaluation

The ready-to-use compositions were applied to yak hair swatches weighing about 1.5 grams each using a brush to thoroughly and uniformly coat the swatches. Two swatches per composition were treated. The compositions were applied to the swatches for about 3 minutes and rinsed with cool tap water.

Each swatch colored with each composition was shampooed with Post Color Professional shampoo for about 30 seconds. The shampoo was removed by rinsing with cool tap water for about 1 minute and dried with a hairdryer at low temperature for about 5-7 minutes.

Yak hair was used because of its pure white color, which enables color deposit to be more easily assessed.

Colorimetric measurements were performed on the swatches thus obtained using a spectrophotometer Konica Minolta CM-2600d (Illuminant: D65; Illuminating/Viewing System: diffused illumination (d/0), spherical geometry; Observer: 2°).

The chromaticity of the swatches was measured using the CIE 1976-L*a*b* international color notation system. The degree of lightening was determined from the change in L (lightening), a (red), and b (yellow) values. The value L* represents the lightness of the shade obtained. The higher this value, the lighter the shade. For each swatch 10 separate measurements were carried out. The results are indicated in Table 2.

TABLE 2

Colorimetric measurements (L* at 3 minutes)

| Swatch | L* |
|---|---|
| C1 | 34.28 |
| C2 | 36.45 |
| C3 | 32.52 |
| CE1 | 39.16 |
| CE3 | 40.72 |

These results shows that the hair yak swatches colored with compositions C1-C3, (which comprise anionic surfactant and cationic surfactant) showed better color uptake and faster coloring rate than the swatches colored with the comparative compositions CE1 (which only contains anionic surfactant) and CE3 (which contains an amphoteric surfactant).

4. Determination of Ammonia Odor

The ammonia odor was evaluated by 2 experienced and trained panelists. The evaluation was carried out under blind conditions, which means that the persons performing the evaluation did not known which formulation they were evaluating. The average was determined from the individual evaluations.

The ammonia odor was rated in accordance with the following criteria: 0 (not perceptible odor); 1 (very slightly perceptible odor); 2 (slightly perceptible odor); 3 (slightly moderate perceptible odor); 4 (moderate perceptible odor); 5 (strong perceptible odor); 6 (very strong perceptible odor). Based on the experience in evaluating products, a slightly moderate perceptible ammonia odor is acceptable by the panelists.

The evaluation was performed for each dyeing composition (C1, C2, C3, CE1 and CE3) and for each ready-to-use composition stored during 24 hours and during 8 weeks at room temperature (RT). The results are indicated in Table 3 and Table 4.

TABLE 3

Ammonia odor perception (dyeing compositions)

| Composition | Dyeing compositions 24 h RT | Dyeing compositions 8 weeks RT |
|---|---|---|
| C1 | 0.5 | 0.5 |
| C2 | 1.5 | 1 |
| C3 | 0 | 1 |
| CE1 | 0 | 1 |
| CE3 | 3 | 3 |

TABLE 4

Ammonia odor perception (ready-to-use compositions)

| Composition | Ready-to-use composition 24 h RT | Ready-to-use composition 8 weeks RT |
|---|---|---|
| C1 | 0.5 | 2 |
| C2 | 2 | 2 |
| C3 | 0.5 | 0.5 |
| CE1 | 0 | 1 |
| CE3 | 4 | 5 |

These results show that the ammonia odor either in the dyeing compositions C1-C3 or in the ready-to-use compositions was relatively low even after 8 weeks of storage.

5. Viscosity Determination

The rheological properties of the dyeing composition (C1, C2, C3, CE1 and CE3) were determined with a HR-1 Hybrid Rheometer supplied by TA Instruments. The results are indicated in Table 5.

TABLE 5

Complex viscosity measured at 25° C., @0.1 Hz (or 0.12 rad/s)

| Swatch | Viscosity |
|---|---|
| C1 | 6313 |
| C2 | 1696 |
| C3 | 6226 |
| CE1 | 16477 |
| CE3 | 12521 |

These results shows that the dyeing compositions C1-C3 showed lower complex viscosity values than the comparative compositions CE1 and CE3. Despite the fact C1-C3 compositions present lower viscosity complex values, these compositions exhibit low ammonia perception as shown in Tables 3 and 4.

6. Anisotropy Evaluation

About 0.05 grams of each dyeing composition C1 to C3 was placed on a glass slide and observed under an optical microscope (Optical Microscope Nikon Eclipse E200) in polarized light at 200× and 400× magnification. High quantity and well-defined maltese crosses were observed.

From the experimental results, it can be concluded that the dyeing compositions of the disclosure present reduced ammonia odor and, at the same time, a faster color processing. In addition, these dyeing compositions are stable and present suitable optical and rheological properties.

Modifications, which do not affect, alter, change or modify the essential aspects of the compositions and methods described above, are included within the scope of the present disclosure.

The invention claimed is:

1. A composition for dyeing keratin fibers, comprising, in a cosmetically acceptable medium, based on a total weight of the composition:

a) at least one anionic surfactant;

b) at least one cationic surfactant comprising cetrimonium chloride;

c) at least one alkoxylated $C_6$-$C_{24}$ fatty alcohol;

d) at least one $C_6$-$C_{24}$ fatty alcohol;

e) at least one oxidation dye;

f) about 0.1-10 wt. % of ammonia, wherein the ammonia is the only alkalizing agent present in the composition such that the composition is free from carbonates, alkanolamines and $C_1$-$C_4$ alkyl alkanolamines, fatty acid salts thereof, or mixtures thereof, and wherein the composition exhibits optical anisotropy.

2. The dyeing composition according to claim 1, wherein the composition comprises about 0.001-10 wt. % of the at least one oxidation dye, and wherein the composition comprises about 0.2-7.5 wt. % of the ammonia.

3. The dyeing composition according to claim 1, wherein the at least one anionic surfactant is selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof.

4. The dyeing composition according to claim 3, wherein the at least one anionic surfactant is selected from alkyl ether carboxylates, alkyl ether sulfates, olefin sulfonates, and mixtures thereof.

5. The dyeing composition according to claim 1, wherein the at least one cationic surfactant is further selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof.

6. The dyeing composition according to claim 1, wherein the at least one alkoxylated $C_6$-$C_{24}$ fatty alcohol is selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof.

7. The dyeing composition according to claim 1, wherein the at least one $C_6$-$C_{24}$ fatty alcohol is selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof.

8. The dyeing composition according to claim 1, wherein:

a) the at least one anionic surfactant is selected from alkyl ether carboxylates, alkyl sulfates, alkyl ether sulfates, amide ether sulfates, alkyl glyceride sulfates, olefin sulfonates, alkyl-aryl sulfonates, sulfosuccinates, sulfo fatty acid esters, fatty acid isethionates, fatty acid taurides, phosphate esters, acyl glutamates, acyl peptides, acyl sarcosides, and mixtures thereof;

b) the at least one cationic surfactant is further selected from $C_6$-$C_{24}$ alkyl trimethyl quaternary ammonium salts, $C_6$-$C_{24}$ alkyl dimethyl benzyl quaternary ammonium salts, $C_6$-$C_{24}$ dialkyl dimethyl quaternary ammonium salts, and mixtures thereof;

c) the at least one alkoxylated $C_6$-$C_{24}$ fatty alcohol is selected from ethoxylated palmytil (cetyl) alcohol, ethoxylated palmitoyl alcohol, ethoxylated stearyl alcohol, ethoxylated cetearyl alcohol, ethoxylated isostearyl alcohol, ethoxylated 2-octyldodecanol, ethoxylated 2-ethylhexanoyl alcohol, ethoxylated oleyl alcohol, and mixtures thereof;

d) the at least one $C_6$-$C_{24}$ fatty alcohol is selected from palmytil (cetyl) alcohol, palmitoyl alcohol, stearyl alcohol, cetearyl alcohol, isostearyl alcohol, 2-octyldodecanol, 2-ethylhexanoyl alcohol, oleyl alcohol, behenyl alcohol, erucyl alcohol, and mixtures thereof;

e) the composition comprises about 0.001-10 wt. % of the at least one oxidation dye; and f) the composition comprises about 0.2-7.5 wt. % of the ammonia.

9. The dyeing composition according to claim 1, wherein the keratin fibers are human hair.

10. A dyeing composition for dyeing keratin fibers obtained by the process comprising the steps of:

i) adding at least one anionic surfactant, at least one alkoxylated $C_6$-$C_{24}$ fatty alcohol, at least one $C_6$-$C_{24}$ fatty alcohol and at least one oxidation dye to a water phase at a temperature from about 50° C. to about 90° C. and under agitation to form an emulsion;

ii) cooling the emulsion obtained in step (i) to a temperature from about 30° C. to about 50° C. and under agitation; and iii) adding at least one cationic surfactant and ammonia to the emulsion obtained in step (ii) under agitation, the at least one cationic surfactant comprising cetrimonium chloride, wherein the dyeing composition includes about 0.1-10 wt. % of ammonia, wherein the ammonia is the only alkalizing agent present in the composition such that the composition is free from carbonates, alkanolamines and C1-C4 alkyl alkanolamines, fatty acid salts thereof, or mixtures thereof, and wherein the composition exhibits optical anisotropy.

11. A multi-compartment device for dyeing keratin fibers comprising at least two compartments packaged separate from one another, wherein one compartment comprises the composition for dyeing keratin fibers of claim 1; and a second compartment comprises a hydrogen peroxide composition.

* * * * *